(12) United States Patent
Bhatt et al.

(10) Patent No.: US 8,623,844 B2
(45) Date of Patent: Jan. 7, 2014

(54) FOSAPREPITANT DIMEGLUMINE INTERMEDIATE, NEUTRAL FOSAPREPITANT, AND AMORPHOUS FOSAPREPITANT DIMEGLUMINE AND PROCESSES FOR THEIR PREPARATIONS

(76) Inventors: Navin Ganesh Bhatt, Navi Mumbai (IN); Nikhil Rasiklal Trivedi, Navi Mumbai (IN); Mahesh Khedekar, Thane (IN); Sukumar Sinha, Navi Mumbai (IN); Mubeen Ahmed Khan, Navi Mumbai (IN); Ramjilal Yadav, Navi Mumbai (IN)

( * ) Notice: Subject to any disclaimer, the term of this patent is extended or adjusted under 35 U.S.C. 154(b) by 239 days.

(21) Appl. No.: 13/003,885

(22) PCT Filed: Jul. 17, 2009

(86) PCT No.: PCT/IN2009/000408
§ 371 (c)(1),
(2), (4) Date: Jan. 13, 2011

(87) PCT Pub. No.: WO2010/018595
PCT Pub. Date: Feb. 18, 2010

(65) Prior Publication Data
US 2011/0130366 A1    Jun. 2, 2011

(30) Foreign Application Priority Data

Jul. 17, 2008 (IN) .......................... 1510/MUM/2008
Oct. 8, 2008 (IN) .......................... 2154/MUM/2008
Mar. 24, 2009 (IN) .......................... 690/MUM/2009

(51) Int. Cl.
*A61K 31/675* (2006.01)
*C07D 413/02* (2006.01)

(52) U.S. Cl.
USPC .............................................. 514/90; 544/132

(58) Field of Classification Search
None
See application file for complete search history.

(56) References Cited

U.S. PATENT DOCUMENTS 5,691,336 A    11/1997    Dorn et al.
2007/0265442 A1    11/2007    McNamara et al.

FOREIGN PATENT DOCUMENTS

WO    2006/60110 A    8/2006

OTHER PUBLICATIONS

J. J. Hale et al., "Phosphorylated Morpholine Acetal Human Neurokinin-1 Receptor Antagonists as Water-Soluble Prodrugs", J. Med. Chem., 2000, vol. 43, pp. 1234-1241.

*Primary Examiner* — Jason M Nolan
*Assistant Examiner* — Ana Z Muresan
(74) *Attorney, Agent, or Firm* — M. Carmen & Associates, PLLC

(57) ABSTRACT

The present invention generally relates to a process for the preparation of fosaprepitant dimeglumine intermediate and its use in the preparation of fosaprepitant dimeglumine; to a neutral form of fosaprepitant in a solid state and processes for the preparation thereof; and to a stable amorphous fosaprepitant dimeglumine, having a stability at temperatures of about 2° C. to about 8° C. and at a relative humidity below at least 60%; and a process for the preparation thereof.

12 Claims, 7 Drawing Sheets

FOSAPREPITANT DIMEGLUMINE INTERMEDIATE, NEUTRAL FOSAPREPITANT, AND AMORPHOUS FOSAPREPITANT DIMEGLUMINE AND PROCESSES FOR THEIR PREPARATIONS

PRIORITY

This application is a 35 U.S.C. 371 National Stage Filing of International Application No. PCT/IN2009/000408, filed Jul. 17, 2009, which claims priority under 35 U.S.C. 119 (a-d) to IN 1510/MUM/2008 filed on Jul. 17, 2008; IN 2154/MUM/2008 filed on Oct. 8, 2008; and IN 690/MUM/2009 filed on Mar. 24, 2009, the contents of each of which are incorporated by reference herein.

BACKGROUND OF THE INVENTION

1. Technical Field

The present invention generally relates to a process for the preparation of a fosaprepitant dimeglumine intermediate and its use in the preparation of fosaprepitant dimeglumine; to a neutral form of fosaprepitant, more specifically in a solid state and processes for the preparation thereof; and to a stable amorphous fosaprepitant dimeglumine and a process for the preparation thereof.

2. Description of the Related Art

Fosaprepitant dimeglumine is approved for the treatment of emesis, nausea, cancer therapy toxicity and is available in the market by brand name EMEND® in the US and IVEMEND® in Europe, with the dosage strength 115 mg equivalent base.

Fosaprepitant dimeglumine is chemically known as 1-deoxy-1-(methyl amino)-D-glucitol[3-[[(2R,3S)-2-[(1R)-1-[3,5-bis(trifluoromethyl)phenyl]-ethoxy]-3-(4-fluorophenyl)-4-morpholinyl]methyl]-2,5-dihydro-5-oxo-1H-1,2,4-triazol-1-yl]phosphonate (2:1) (salt) and is structurally represented by formula (I):

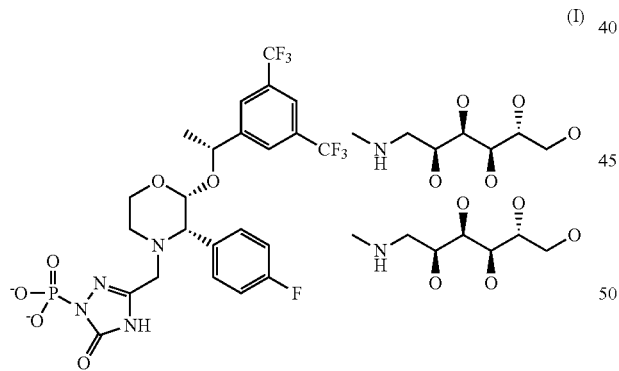

(I)

US Publication 20070265442 describes a process for the preparation of fosaprepitant dimeglumine using monobenzyl ester fosaprepitant as an intermediate; but it neither discloses nor characterizes the polymorph obtained.

U.S. Pat. No. 5,691,336 describes morpholine compounds including fosaprepitant and its pharmaceutically acceptable salts thereof. The U.S. '336 patent exemplifies the process for the preparation of fosaprepitant dimeglumine as amorphous powder by lyophilization of an aqueous solution.

Fosaprepitant in solid state, isolated form has not been reported in the literature as of date. Also polymorphs of fosaprepitant neutral form have not been reported in the literature.

The difference in the physical properties of different solid state forms results from the orientation and intermolecular interactions of adjacent molecules or complexes in the bulk solid. Accordingly, polymorphs are distinct solids sharing the same molecular formula, while having distinct physical properties, which may be advantageous relative to other solid state forms of the same compound or complex.

The discovery of fosaprepitant in solid state provides a new opportunity to improve the performance of the active pharmaceutical ingredient (API), fosaprepitant dimeglumine or other salts, by producing solid forms of pure fosaprepitant having improved characteristics, such as stability, flowability, and solubility. The solid state form of a compound may also affect its behavior on compaction and its storage stability.

Thus, there is a need in the art to provide fosaprepitant in solid state and possible polymorphic forms of fosaprepitant. The availability of neutral fosaprepitant in solid form would be an added advantage in the preparation of pharmaceutically acceptable salts of fosaprepitant such as fosaprepitant dimeglumine useful in the preparation of pharmaceutical formulations, particularly parental dosage forms for the treatment of emesis, nausea, cancer therapy toxicity.

SUMMARY OF THE INVENTION

The present invention generally relates to a process for the preparation of a fosaprepitant dimeglumine intermediate and its use in the preparation of fosaprepitant dimeglumine.

In a first embodiment, the present invention provides a process for the preparation of dibenzyl ester fosaprepitant, comprising:

a) providing a solution of dibenzyl ester fosaprepitant in a solvent or a mixture of solvents;
b) adding an anti-solvent to the solution to precipitate the solid;
c) recovering the precipitated dibenzyl ester fosaprepitant solid and drying.

In a second embodiment, the present invention provides a process for the preparation of a stable dibenzyl{3-[2(R)-[(1R)-1-[3,5-bis(trifluoromethyl)phenyl]ethoxy]-3(S)-(4-fluorophenyl) morpholin-4-yl]-5-oxo-4,5-dihydro-[1,2,4]-triazol-1-yl}phosphonic acid of formula (II) (hereinafter referred as dibenzyl ester fosaprepitant).

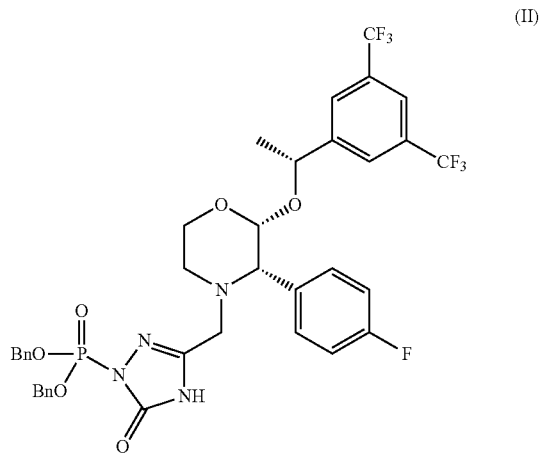 [SMILES: C[C@@H](O[C@H]1OCCN(Cc2nn(P(=O)(OCc3ccccc3)OCc3ccccc3)c(=O)[nH]2)[C@H]1c1ccc(F)cc1)c1cc(C(F)(F)F)cc(C(F)(F)F)c1]

(II)

In a third embodiment, the present invention provides an isolated, solid stable dibenzyl ester fosaprepitant.

In a fourth embodiment, the present invention provides a crystalline form of a dibenzyl ester fosaprepitant.

In a fifth embodiment, the present invention provides a crystalline form of dibenzyl ester fosaprepitant), having an X-ray powder diffraction (XRPD) pattern, which is substantially in accordance with FIG. 1.

In a sixth embodiment, the present invention provides a crystalline form of dibenzyl ester fosaprepitant, having differential scanning calorimetry (DSC) thermogram which is substantially in accordance with FIG. 2.

In a seventh embodiment, the present invention provides an isolated dibenzyl ester fosaprepitant having less than about 1.5 area % of monobenzyl{3-[2(R)-[(1R)-1-[3,5-bis(trifluoromethyl)phenyl]ethoxy]-3(S)-(4-fluorophenyl)morpholin-4-yl}-5-oxo-4,5-dihydro-[1,2,4]-triazol-1-yl}phosphonic acid of formula (III), as measured by high performance liquid chromatography (HPLC).

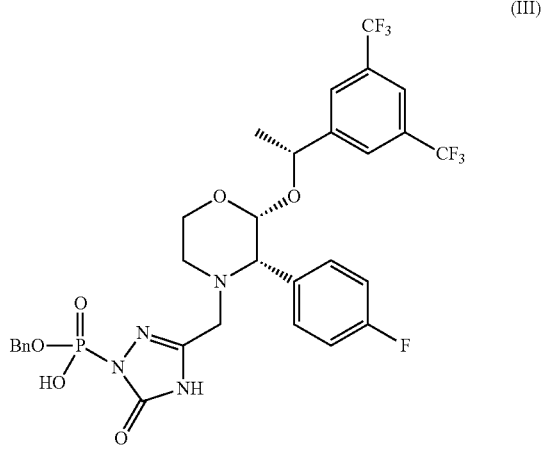 [SMILES: C[C@@H](O[C@H]1OCCN(Cc2nn(P(=O)(O)OCc3ccccc3)c(=O)[nH]2)[C@H]1c1ccc(F)cc1)c1cc(C(F)(F)F)cc(C(F)(F)F)c1]

(III)

In an eighth embodiment, the present invention provides an isolated dibenzyl ester fosaprepitant, having less than about 0.5% of monobenzyl{3-[2(R)-[(1R)-1[3,5-bis(trifluoromethyl)phenyl]ethoxy]-3(S)-(4-fluorophenyl)morpholin-4-yl}-5-oxo-4,5-dihydro-[1,2,4]-triazol-1-yl}phosphonic acid of formula (III)), as measured by high performance liquid chromatography (HPLC).

In a ninth embodiment, the present invention provides a process for the purification of fosaprepitant dimeglumine, comprising:
a) providing a solution of dibenzyl ester fosaprepitant in a solvent or mixture of solvents;
b) subjecting the solution to hydrogenation in the presence of palladium-carbon and N-methyl-D-glucamine; and
c) recovering the fosaprepitant dimeglumine with desired purity by recrystallization.

In a tenth embodiment, the present invention provides fosaprepitant dimeglumine, obtained by the process herein described, having at least about 99.7% purity with an aprepitant content, which is not more than (NMT) about 0.15%, as measured by high performance liquid chromatography (HPLC).

In an eleventh embodiment, the present invention provides fosaprepitant dimeglumine having at least about 99.7% purity, with an aprepitant content, which is not more than (NMT) about 0.15%, and any other impurity, which is NMT about 0.05%, as measured by high performance liquid chromatography (HPLC).

In a twelfth embodiment, the present invention provides fosaprepitant dimeglumine having at least about 99.7% purity, with an aprepitant content, which is NMT about 0.15%, a dibenzylester fosaprepitant content, which is below detection limit; and a monobenzyl ester fosaprepitant content, which is below detection limit, as measured by high performance liquid chromatography (HPLC).

In a thirteenth embodiment, the present invention relates to a process for the preparation of a neutral form of fosaprepitant, comprising: a) providing a solution of fosaprepitant salt in a mixture of water and an organic solvent; b) adding an acid to the solution in a) to a pH of about 1 to about 5; c) recovering the desired neutral form of fosaprepitant.

In a fourteenth embodiment, the present invention relates to a neutral form of fosaprepitant.

The present invention provides a neutral form of fosaprepitant characterized by its X-ray powder diffraction (XRPD) pattern, which is substantially in accordance with FIG. 3.

The present invention provides a neutral form of fosaprepitant characterized by a DSC thermogram in accordance with FIG. 4, with a sharp endotherm at 207° C. with onset at about 200.79° C. and endset at about 212.92° C.

The present invention provides that the neutral form, which is in the solid state form, of fosaprepitant, obtained by the process described herein, may optionally be converted into a pharmaceutically acceptable salt of fosaprepitant by any method known to one of ordinary skill in the art. A preferred pharmaceutically acceptable salt is the fosaprepitant dimeglumine. The dimeglumine salt may be prepared by a method including, but not limited to, reacting the neutral form of fosaprepitant with N-methyl-D-glucamine. Typically, the fosaprepitant is dissolved in an organic solvent and combined with a solution of acid or base used to obtain the desired salt of fosaprepitant.

In a fifteenth embodiment, the present invention relates to a stable amorphous fosaprepitant dimeglumine.

The present invention relates to a stable amorphous fosaprepitant dimeglumine, having stability at temperatures of about 2° C. to about 8° C. and at a relative humidity below at least 60%.

In one aspect, the present invention provides a stable amorphous fosaprepitant dimeglumine characterized by X-ray powder diffraction (XRPD) spectrum, which is substantially in accordance with FIG. 5.

In another aspect, the present invention provides a stable amorphous fosaprepitant dimeglumine further characterized by differential scanning calorimetry (DSC) endotherm curve which is substantially in accordance with FIG. 6.

In yet another aspect, the present invention provides a stable amorphous fosaprepitant dimeglumine further characterized by stability data, which are a series of XRPD spectra, which are substantially in accordance with FIG. 7.

The present invention relates to a process for the preparation of a stable amorphous fosaprepitant dimeglumine.

The present invention relates to a process for the preparation of a stable amorphous fosaprepitant dimeglumine, having stability at temperatures of about 2° C. to about 8° C. and at a relative humidity below at least 60%.

In another aspect, the present invention provides a process for the preparation of a stable amorphous fosaprepitant dimeglumine, having a stability at temperatures of about 2° C. to about 8° C. and at a relative humidity below at least 60%; comprising:
a) preparing a solution of fosaprepitant dimeglumine in one or more solvents or their aqueous mixtures thereof; and optionally treating with activated carbon;

b) precipitating a solid by adding an antisolvent to the solution in a); and c) recovering the solid in b) to obtain the stable amorphous fosaprepitant dimeglumine.

In yet another aspect, the present invention relates to pharmaceutical compositions comprising stable amorphous fosaprepitant dimeglumine and at least one pharmaceutically acceptable carrier.

DETAILED DESCRIPTION OF THE INVENTION

Figure 1:
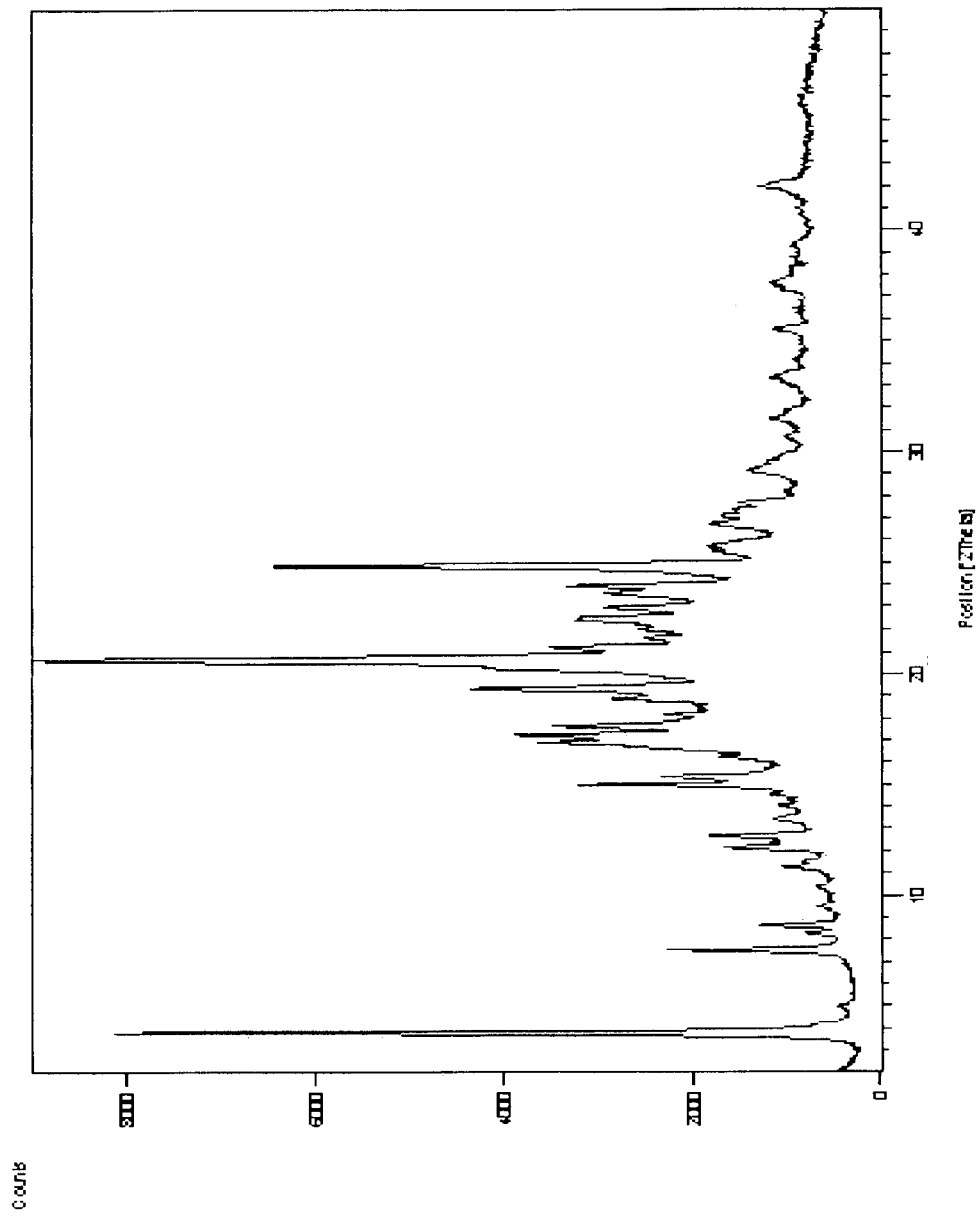
FIG. 1: X-ray Powder Diffraction (XRPD) pattern of dibenzyl ester fosaprepitant, as prepared by Example 1.

Fosaprepitant in solid state, isolated form has not been reported in the literature as of date. Also polymorphs of fosaprepitant neutral form have not been reported in the literature.

The difference in the physical properties of different solid state forms results from the orientation and intermolecular interactions of adjacent molecules or complexes in the bulk solid. Accordingly, polymorphs are distinct solids sharing the same molecular formula while having distinct physical properties, which may be advantageous relative to other solid state forms of the same compound or complex.

The discovery of fosaprepitant in solid state provides a new opportunity to improve the performance of the active pharmaceutical ingredient (API), fosaprepitant dimeglumine or other salts, by producing solid forms of pure fosaprepitant having improved characteristics, such as stability, flowability, and solubility. The solid state form of a compound may also affect its behavior on compaction and its storage stability.

The present invention provides a process for the preparation of a fosaprepitant dimeglumine intermediate and its use in the preparation of fosaprepitant dimeglumine. The fosaprepitant dimeglumine intermediate of the present invention is a stable dibenzyl ester fosaprepitant. The stable dibenzyl ester fosaprepitant is present in a crystalline form and may be used in the process for the purification of fosaprepitant dimeglumine of formula (I).

The present invention provides the preparation of dibenzyl ester fosaprepitant, comprising:

a) providing a solution of dibenzyl ester fosaprepitant in a solvent or a mixture of solvents;

b) adding an anti-solvent to the solution to precipitate the solid;

c) recovering the precipitated solid and drying to obtain dibenzyl ester fosaprepitant.

The solvent(s) that can be used for dissolution in a) of the process directly described above, is selected from ethyl acetate, n-propyl acetate, isopropyl acetate, n-butyl acetate, isobutyl acetate, tertiary butyl acetate or mixtures thereof. Preferably ethyl acetate.

The ratio of the process above of dibenzyl ester fosaprepitant to a solvent is about 1:2 to 1:10, preferably, 1:3.

The temperature for dissolution can range from about 25° C. to about 100° C. or reflux temperatures of the solvents used, preferably at about 30° C.

The time period for dissolution can range from about 30 minutes to about 5 hours, preferably about 1 hour.

The ratio of anti-solvent used in b) above to the solution in a) is about 1:4 to 1:10, preferably 1:5.

The solution obtained is optionally filtered by using conventional filtration techniques known in the art, including filtration through celite or diatomaceous earth to separate the extraneous matter present or formed in the solution.

The anti-solvent(s) that can be used to precipitate the solid is selected from hydrocarbon solvents like n-pentane, n-hexane, n-heptane, cyclohexane or mixtures thereof, preferably cyclohexane.

The temperature range for precipitation of solid can be from about −10° C. to about 35° C., preferably from about 25° C. to about 30° C.

The time period for complete precipitation of solid can range from about 30 minutes to about 5 hours, preferably about 2 hours.

The present invention provides that the obtained dibenzyl ester fosaprepitant can be dried under conditions, which can avoid degradation of the product, at temperatures that can be from about 20° C. to about 35° C., preferably from about 25° C. to about 30°, and at reduced pressure of about 5 mbar to about 20 mbar, preferably about 10 mbar, for a period of about 1 hour to about 48 hours, preferably about 12 hours.

The present invention provides a stable dibenzyl ester fosaprepitant, which is dibenzyl{3-[2(R)-[(1R)-1-[3,5-bis(trifluoromethyl)phenyl]ethoxy]-3(S)-(4-fluorophenyl)morpholin-4-yl}-5-oxo-4,5-dihydro-[1,2,4]-triazol-1-yl}phosphonic acid of formula (II).

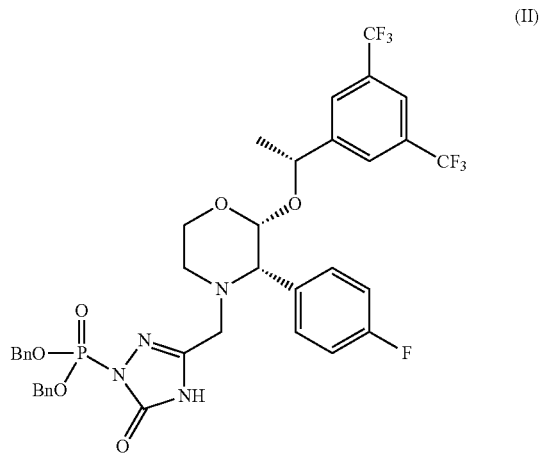 [SMILES: C[C@@H](O[C@H]1OCCN(Cc2nn(P(=O)(OCc3ccccc3)OCc3ccccc3)c(=O)[nH]2)[C@H]1c1ccc(F)cc1)c1cc(C(F)(F)F)cc(C(F)(F)F)c1]

The present invention provides that the dibenzyl ester fosaprepitant is crystalline.

The crystalline form of dibenzyl ester fosaprepitant, which is prepared as in Example 1, is characterized by its X-ray powder diffraction (XRPD) pattern, which is substantially in accordance with FIG. 1.

The present invention provides a crystalline form of dibenzyl ester fosaprepitant, characterized by a XRPD pattern with peaks at about: 3.8, 7.5, 15.0, 16.9, 17.3, 17.6, 19.3, 20.6, 21.2, 23.9, and 24.8±0.2° 2θ.

X-ray powder diffraction measurement was performed on a Philips X'pert PRO Diffractometer using Cu Kα radiation (Cu Kα1=1.54060 Å). The X-ray source is operated at 45 kV and 40 mA. Spectra are recorded at start angle from 2° to 50° 2θ, a step size 0.0167° with times per steps of 50 seconds.

Figure 2:
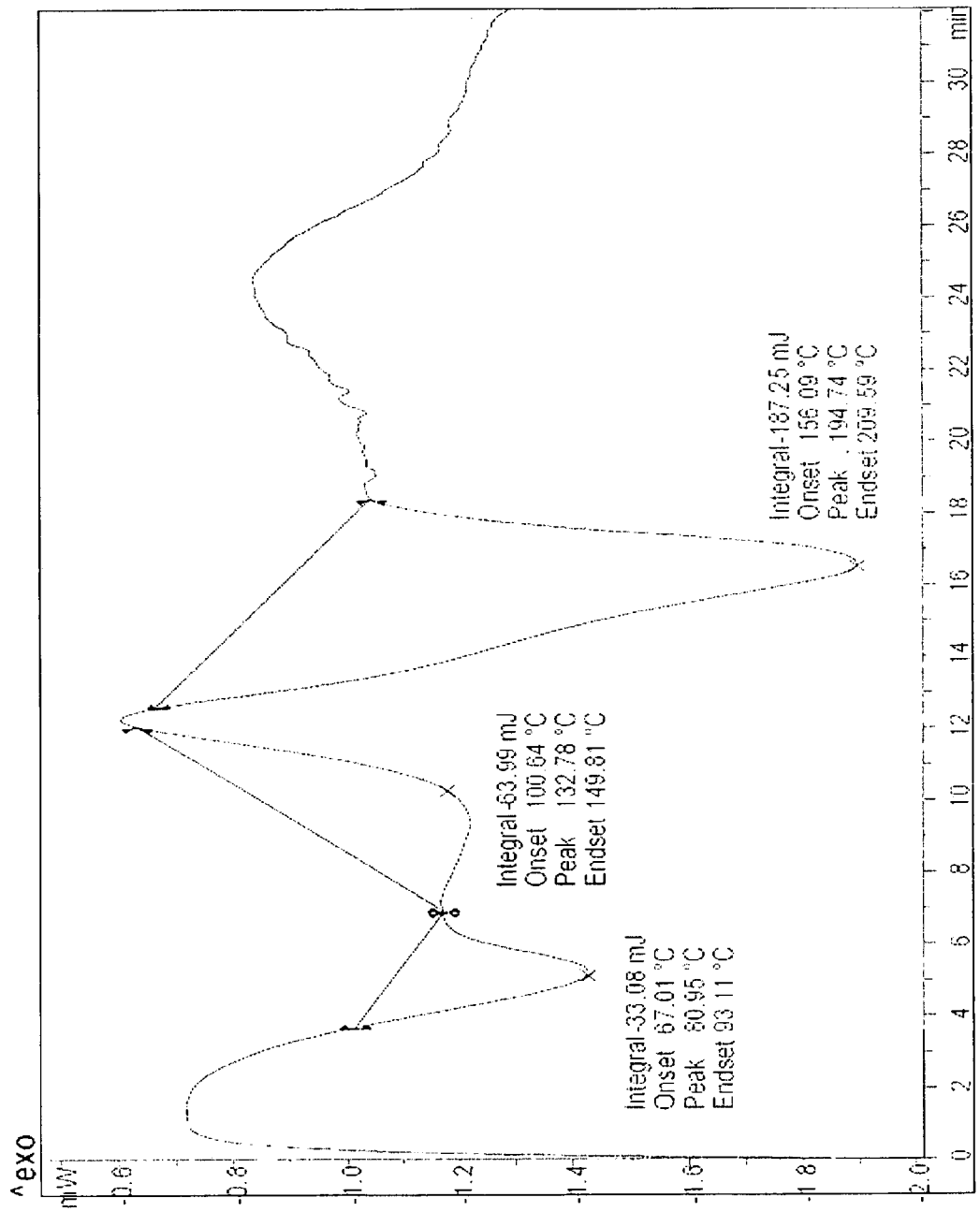
FIG. 2: Differential Scanning calorimetry (DSC) thermogram of dibenzyl ester fosaprepitant, as prepared by Example 1.

The present invention provides that the crystalline form of dibenzyl ester fosaprepitant, which is prepared as in Example 1, is characterized by differential scanning calorimetry (DSC) thermogram with a sharp endotherm at 194.74° C. with onset at about 156.09° C. and end set at about 209.59° C., which is substantially in accordance with FIG. 2.

Differential scanning calorimetry (DSC) is measured by taking approximately 1-5 mg of sample, which was accurately weighed into an aluminum DSC pan with lid. The sample was placed then into a Mettler Toledo DSC822$^e$ equipped with a liquid nitrogen cooling unit and allowed to equilibrate at 30° C. until stable heat flow response was seen. A dry nitrogen purge gas at a flow rate of 50 ml/min was used to produce the inert atmosphere and prevent oxidation of the sample during heating. The sample was scanned from 30° C.-350° C. at a rate of 10° C./min and the resulting heat flow response was measured against temperature.

The present invention provides for dibenzyl ester fosaprepitant having less than about 1.5 area % of monobenzyl{3-[2(R)-[(1R)-1-[3,5-bis(trifluoromethyl)phenyl]ethoxy]-3(S)-(4-fluorophenyl)morpholin-4-yl}-5-oxo-4,5-dihydro-[1,2,4]-triazol-1-yl}phosphonic acid of formula (III).

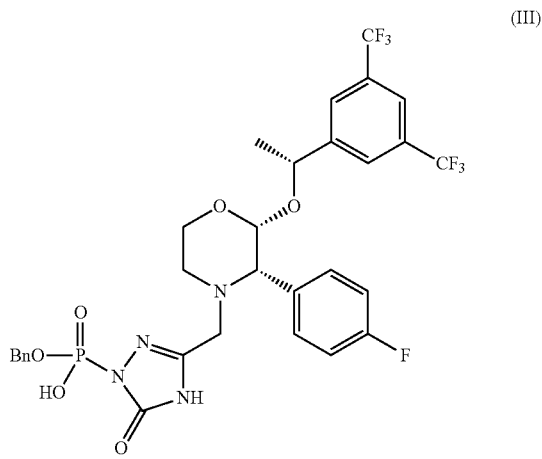 [SMILES: C[C@@H](O[C@H]1OCCN(Cc2nn(P(=O)(O)OCc3ccccc3)c(=O)[nH]2)[C@H]1c1ccc(F)cc1)c1cc(C(F)(F)F)cc(C(F)(F)F)c1]

The present invention provides dibenzyl ester fosaprepitant having less than about 1.5 area % of monobenzyl{3-[2(R)-[(1R)-1-[3,5-bis(trifluoromethyl)phenyl]ethoxy]-3(S)-(4-fluorophenyl)morpholin-4-yl}-5-oxo-4,5-dihydro-[1,2,4]-triazol-1-yl}phosphonic acid of formula (III).

The present invention provides dibenzyl ester fosaprepitant having less than about 0.5 area % of monobenzyl{3-[2(R)-[(1R)-1-[3,5-bis(trifluoromethyl)phenyl]ethoxy]-3(S)-(4-fluorophenyl)morpholin-4-yl}-5-oxo-4,5-dihydro-[1,2,4]-triazol-1-yl}phosphonic acid of formula (III).

The present invention provides a process for the purification of fosaprepitant dimeglumine, comprising:
a) providing a solution of dibenzyl ester fosaprepitant, prepared by the process previously herein described, in a solvent or mixture of solvents;
b) subjecting the solution of (a) to hydrogenation in the presence of palladium-carbon and N-methyl-D-glucamine; and
c) precipitating the fosaprepitant dimeglumine by adding the solution of (b) to anti-solvent(s);
d) recovering the fosaprepitant dimeglumine with desired purity by recrystallization.

In a) of the process directly described above, the volume of solvent or mixture of solvents relative to the dibenzyl ester fosaprepitant is about 9 volumes to about 15 volumes. Preferably, about 10 volumes.

The percent of Pd in Pd—C used for hydrogenation ranges from about 5% w/w to about 20% w/w, preferably about 10% w/w.

The amount of N-methyl-D-glucamine used relative to the dibenzyl ester fosaprepitant ranges from about 1:0.55 w/w to 1:2 w/w. Preferably, about 1:0.6 w/w.

In b) above, the volume of anti-solvent relative to the dibenzyl ester fosaprepitant is about 9 volumes to about 35 volumes. Preferably, about 10 volumes.

The fosaprepitant dimeglumine can be recovered by re-crystallization techniques known in the art, preferably filtration.

The present invention provides the dibenzyl ester fosaprepitant used in making a solution of fosaprepitant dimeglumine in a solvent or a solvent mixture is the solid crystalline dibenzyl ester fosaprepitant obtained by the process described herein.

The solvent(s) that can be used in (a) of the process for the purification of fosaprepitant dimeglumine, for dissolution is selected from alcohols including methanol, ethanol, isopropanol or mixtures thereof; and aprotic polar solvents including but are not limited to N,N-dimethylformamide (DMF), dimethyl sulfoxide (DMSO) or mixtures thereof or their aqueous mixtures. Preferably methanol.

The temperatures for dissolution can range from about 25° C. to about 100° C. or reflux temperatures of the solvents used. Preferably at about 30° C.

Hydrogenation is carried out using hydrogenation pressure of about 50 psi to about 150 psi, preferably at about 100 psi, at about 25° C. to about 75° C., preferably at about 30° C., for a period of about 30 minutes to about 10 hours, preferably 1 hour.

The anti-solvent(s) that can be used for precipitation of solid in c) of the process directly described above is selected from acetone, methyl ethyl ketone, methyl isobutyl ketone, methyl isopropyl ketone and methyltertbutylketone or mixtures thereof or their aqueous mixtures. Preferably acetone.

Recovery of fosaprepitant dimeglumine can be achieved by any conventional methods known in the art, for example, by filtration. The process of the present invention for the purification of fosaprepitant dimeglumine may optionally include further drying of the product obtained from the solution by any method known in the art.

The obtained fosaprepitant dimeglumine can be dried under conditions which avoid degradation of the product, and at temperatures that can be from about 25° C. to about 35° C., preferably at 30° C., and at reduced pressure of about 5 mbar to about 20 mbar, preferably 10 mbar, for a period of about 1 hour to about 72 hours, preferably for about 48 hours.

Crystallization may also be induced by decreasing the solubility of fosaprepitant dimeglumine, e.g. by cooling the mixture, or by evaporation of some of the solvents, where the crystals of the isolated fosaprepitant dimeglumine can be made. The crystallization may start spontaneously. The crystals of the desired form of fosaprepitant dimeglumine can be used, preferably, in inducing crystallization.

The present invention provides fosaprepitant dimeglumine produced by the process of purification of the present invention is characterized by a purity of at least about 99 area % as measured by HPLC, preferably at least about 99.5 area %, as measured by HPLC.

The present invention provides pure fosaprepitant dimeglumine characterized by HPLC purity of at least about 99.7 area % and containing aprepitant not more than (NMT) about 0.15%.

The present invention provides fosaprepitant dimeglumine characterized by HPLC purity of at least about 99.7 area % and containing aprepitant NMT about 0.15% and any other individual impurity NMT about 0.05%.

The present invention provides fosaprepitant dimeglumine characterized by HPLC purity of at least about 99.7 area % with aprepitant NMT about 0.15% and dibenzylester fosaprepitant below detection limit; monobenzyl ester fosaprepitant below detection limited.

The present invention provides a fosaprepitant dimeglumine, obtained by the process described above, having a residual organic solvent less than about the amount recommended for pharmaceutical products, as set forth for example in ICH guidelines and U.S. pharmacopoeia; i.e., less than about 3000 ppm of acetone, less than about 1000 ppm of ethyl acetate and isopropyl alcohol, methanol, cyclohexane, ethanol, less than about 100 ppm of isopropyl ether, tetrahydrofuran and toluene.

The isolation of intermediates of fosaprepitant in solid state and discovery of new, stable polymorphs provides an opportunity to improve the performance of the active pharmaceutical ingredient (API), fosaprepitant dimeglumine, by producing solid forms of fosaprepitant intermediates in pure form having improved characteristics, such as stability and solubility. The use of isolated solid form of intermediate compounds would provide a way to achieve the final fosaprepitant dimeglumine in pharmaceutically acceptable purity and provides it in a form that is convenient to use, for example, suitable for compaction and having good storage stability.

US Publication 20070265442 describes a process for the preparation of fosaprepitant dimeglumine using monobenzyl ester fosaprepitant as an intermediate; however, this route leads to the formation of an unstable amorphous dibenzyl ester fosaprepitant.

Thus, there is a need in the art to provide intermediates of fosaprepitant in solid state. The availability of intermediates of fosaprepitant in solid form would be an added advantage in the preparation of fosaprepitant or its pharmaceutically acceptable salts such as fosaprepitant dimeglumine useful in the preparation of pharmaceutical formulations particularly parental dosage forms for the treatment of Emesis, nausea, cancer therapy toxicity.

The present invention relates to a neutral form of fosaprepitant in a solid state and processes for the preparation thereof.

Figure 3:
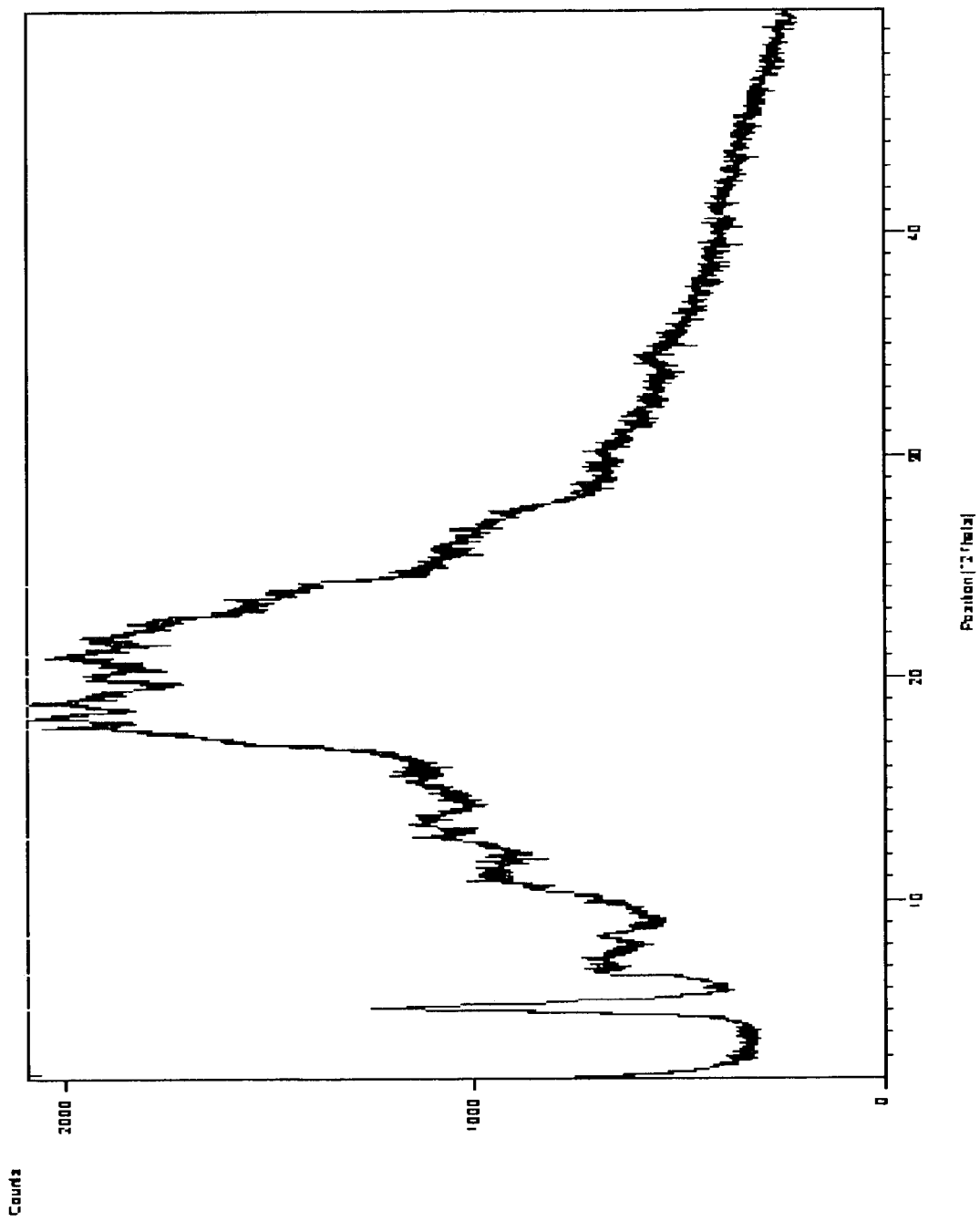
FIG. 3: X-ray Powder Diffraction (XRPD) pattern of fosaprepitant neutral form, as prepared by Example 4.

The present invention relates to a neutral form of fosaprepitant characterized by its X-ray powder diffraction (XRPD) pattern, which is substantially in accordance with FIG. 3.

Figure 4:
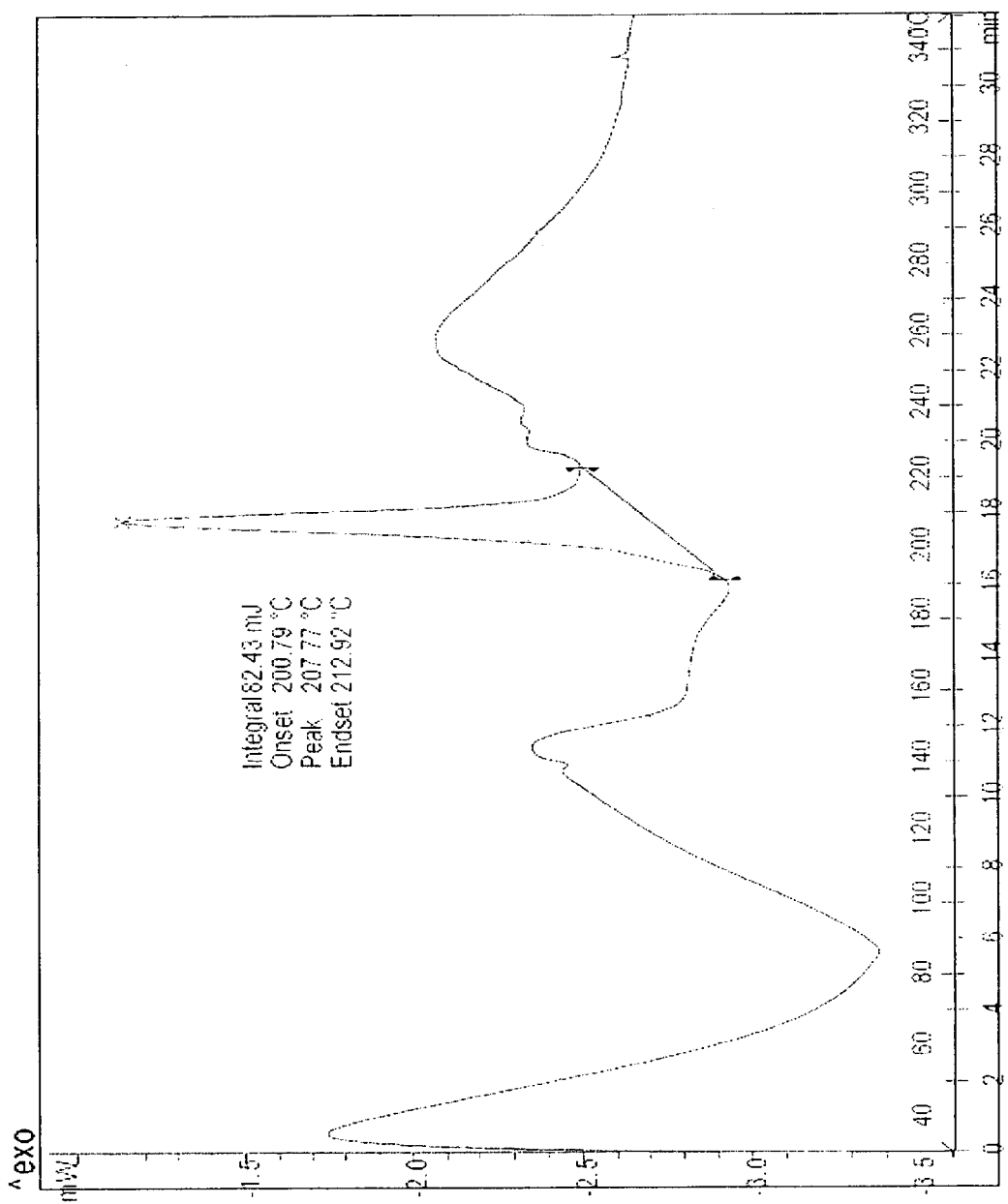
FIG. 4: Differential Scanning calorimetry (DSC) thermogram of fosaprepitant neutral form, as prepared by Example 4.

The present invention relates to a neutral form of fosaprepitant characterized by DSC thermogram in accordance with FIG. 4, and has a sharp endotherm at 207° C. with onset at about 200.79° C. and endset at about 212.92° C.

The (DSC) thermogram is measured at the rate of 10° C./min. in the range of about 30° C. to 350° C. using a Mettler Toledo instrument.

The present invention relates to a process for preparing a neutral form of fosaprepitant, the process comprising:
a) providing a solution of fosaprepitant salt in a mixture of water and an organic solvent;
b) adding an acid to the solution in a) to a pH of about 1 to about 5;
c) recovering the desired neutral form of fosaprepitant in b);
where the organic solvent comprises alcohols selected from methanol, ethanol, n-propanol, isopropanol, n-butanol, isobutanol, and tertiary butyl alcohol, preferably methanol; and the acid comprises mineral acids selected from hydrochloric acid, hydrobromic acid, preferably hydrochloric acid.

The solution of fosaprepitant salt can be obtained by dissolving a fosaprepitant salt in a mixture of water and suitable organic solvent(s). The solvent(s) that can be used in combination with water include but are not limited to alcohols, ketones, nitriles, aprotic polar solvents or mixtures thereof; where the alcohols include but are not limited to methanol, ethanol, n-propanol, isopropanol, n-butanol, isobutanol, and tertiary butyl alcohol and the like, preferably methanol; the ketones include but are not limited to acetone, methyl ethyl ketone, methyl isobutyl ketone, 2-butanone and the like, preferably acetone; nitriles include but are not limited to acetonitrile, propionitrile and the like, preferably acetonitrile; aprotic polar solvents may include N,N-dimethylformamide (DMF), dimethylsulfoxide (DMSO), N,N-dimethylacetamide (DMA) and the like; or mixtures thereof in various proportions without limitation.

The organic solvent(s) is more preferably water miscible solvent(s) like, acetone, acetonitrile or a lower alkyl alcohol.

The salt of fosaprepitant can be selected from base salts like ammonium salts, alkali metal salts like sodium, lithium and potassium salts, alkaline earth metal salts such as aluminum, calcium and magnesium salts, salts with organic bases like dicyclohexylamine salts, N-methyl-D-glucamine or mixtures thereof.

The starting material of the process as described above, is preferably a water soluble salt of fosaprepitant, for example a basic salt, particularly a dimeglumine salt. The starting material used in the process described herein, can be a fosaprepitant salt of any polymorphic form known in the art.

The temperature for getting clear and homogenous solution in a) can range from about 25° C. to about 75° C. or to about the boiling point or reflux temperature of the solvent/s used.

The ratio of the fosaprepitant salt to water to organic solvent is from 1:10:10 to about 1:60:60, preferably, 1:20:20.

The solution obtained in a) is optionally filtered through diatomaceous earth to separate the extraneous matter present or formed in the solution, or, by using conventional filtration techniques known in the art.

The acid added to the solution may be mineral acids such as hydrochloric acid, hydrobromic acid, preferably aqueous hydrochloric acid. The pH of the final solution may be from about 1 to about 5, preferably at pH of about 1.

Recovery of the desired neutral form of fosaprepitant may be achieved by any conventional methods known in the art, including filtration. The process may optionally include further drying of the product obtained from the solution by any method known in the art.

It is desirable to crystallize the target compound. Crystallization may be induced by decreasing the solubility of fosaprepitant, like cooling the solution, or evaporation of some of the solvents, or adding a precipitating solvent or anti-solvent.

Crystallization may also be induced by addition of a solution of an acid to about a pH 1 to about pH 5 that would not degrade the target compound, preferably at pH of about 3 to about 4, where the product undergoes minimum degradation.

The resulting precipitate of neutral fosaprepitant is generally in a solid form substantially in accordance with XRPD (FIG. 3) and DSC (FIG. 4).

When the neutral fosaprepitant is crystallized, the crystals may be separated from the solution, e.g. by filtration or centrifugation, followed by washing with a washing liquid, preferably a solvent or a mixture in which the particular form of neutral fosaprepitant has a very low solubility, for example, an anti-solvent.

The crystals of the desired form of a neutral fosaprepitant, which are isolated as described above, can be used as seeds in the crystallization process. The subsequent crystallization steps may start spontaneously, but it is preferable, when possible, to add seeds of the desired form of neutral fosaprepitant.

The proportion of solvent(s) to product used for washing is from 1:1 to 5:1 by weight, preferably 4:1.

The obtained neutral fosaprepitant can be dried under conditions, which avoid degradation of the product, can be from about 25° C. to about 35° C., preferably at 25° C. to about 30° C. and at reduced pressure of about 5 mbar to about 20 mbar, preferably at about 10 mbar, for about 1 hour to 48 hours, preferably for about 24 hours.

The present invention provides that the neutral form, which is in the solid state form, of fosaprepitant, obtained by the process described herein, may optionally be converted into a pharmaceutically acceptable salt of fosaprepitant by any method known to one of ordinary skill in the art. A preferred pharmaceutically acceptable salt is the fosaprepitant dimeglumine. The dimeglumine salt may be prepared by a method including, but not limited to, reacting the neutral form of fosaprepitant with N-methyl-D-glucamine. Typically, the fosaprepitant is dissolved in an organic solvent and combined with a solution of acid or base used to obtain the desired salt of fosaprepitant.

Fosaprepitant in solid state, in its isolated form has not been reported in the literature as of date. Moreover, the polymorphs of fosaprepitant neutral form have not been reported in the literature.

The difference in the physical properties of different solid state forms results from the orientation and intermolecular interactions of adjacent molecules or complexes in the bulk solid. Accordingly, polymorphs are distinct solids sharing the same molecular formula yet having distinct advantageous physical properties compared to other solid state forms of the same compound or complex.

The solid state form of a compound may affect its behavior on compaction and its storage stability. Fosaprepitant in solid state provides an opportunity to improve the performance of an active pharmaceutical ingredient (API) formulation, fosaprepitant dimeglumine or other salts relative to stability, flowability, and solubility.

Fosaprepitant in solid state would be an added advantage in the preparation of pharmaceutically acceptable salts of fosaprepitant such as fosaprepitant dimeglumine, which is useful in the preparation of pharmaceutical formulations particularly parental dosage forms for the treatment of emesis, nausea, cancer-induced vomiting and nausea.

The process of present invention is simple, efficient, cost effective, ecofriendly, robust, reproducible, commercially viable, industrially feasible to produce the desired amorphous form or crystalline form of fosaprepitant.

Fosaprepitant dimeglumine, by nature, is a hygroscopic and heat sensitive compound, which leads to instability problems. The amorphous fosaprepitant dimeglumine obtained by lyophilization of an aqueous solution as disclosed in the '336 patent suffers from instability. The amorphous fosaprepitant dimeglumine loses its stability upon exposure to normal room temperature, as well as at about 2° C.-8° C. The amorphous fosaprepitant dimeglumine loses its amorphous nature and transforms into crystalline form. Thus, additional stabilizers or carriers are required to make the amorphous fosaprepitant dimeglumine stable immediately upon isolation from the aqueous solution. This, then, would lend difficulty in handling and make it unsuitable for desired pharmaceutical formulations.

It is desirable, when in the amorphous form, that an active pharmaceutical product, retain its form from the time of manufacture to the time it is formulated and consumed by the patient in need thereof. Hence it is essential to provide a stable amorphous form of fosaprepitant dimeglumine.

As discussed above, the present invention provides a stable amorphous fosaprepitant dimeglumine, having stability at temperatures of about 2° C. to about 8° C. and at a relative humidity below at least 60%; and a process for the preparation thereof.

Fosaprepitant dimeglumine, by nature, is a heat and moisture sensitive compound and suffers from instability problems, where it rapidly degrades at normal room temperature, losing its morph.

Polymorphism is the occurrence of different crystalline forms of a single compound and it is a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different x-ray diffraction peaks. Since the solubility of each polymorph may vary, identifying the existence of pharmaceutical polymorphs is essential for providing pharmaceuticals with predicable solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffraction spectroscopy and by other methods such as, infrared spectrometry.

Additionally, polymorphic forms of the same drug substance or active pharmaceutical ingredient, can be administered by itself or formulated as a drug product (also known as the final or finished dosage form), and are well known in the pharmaceutical art to affect, for example, the solubility, stability, flowability, tractability and compressibility of drug substances and the safety and efficacy of drug products.

Towards this end, it has been the endeavor of pharmaceutical scientists to provide amorphous forms of crystalline drug substances, more specifically, thermodynamically stable forms of drug substances, which would have the strengths of the crystalline forms, viz. thermodynamic stability, and those of the amorphous form, viz. enhanced solubility, rapid onset of action and an enhanced bioavailability.

Accordingly, there remains a need to provide amorphous form of fosaprepitant dimeglumine in substantially stable form for use in a pharmaceutical preparation.

The availability of a substantially stable amorphous form of fosaprepitant dimeglumine, having a stability at temperatures of about 2° C. to about 8° C. and at a relative humidity below at least 60%; would add a powerful tool in the treatment of emesis, nausea, cancer-induced nausea and vomiting.

Figure 5:
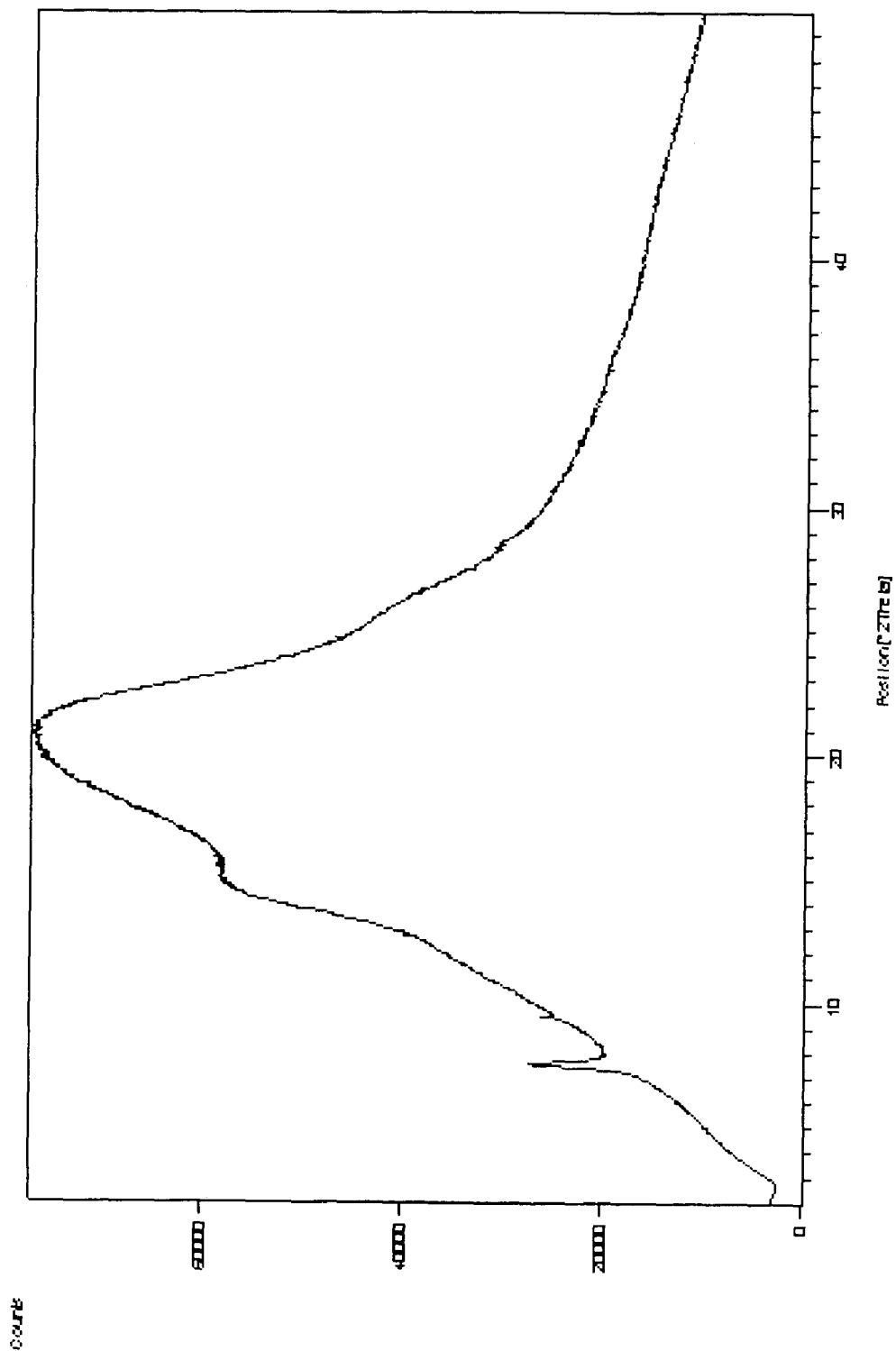
FIG. 5: X-ray Powder Diffraction (XRPD) pattern of a stable amorphous fosaprepitant dimeglumine, as prepared by Example 5.

The present invention provides stable amorphous form of fosaprepitant dimeglumine characterized by X-ray powder diffraction pattern (XPRD) spectrum, which is substantially in accordance with FIG. 5. The stable amorphous form of fosaprepitant dimeglumine may also be characterized by differential scanning calorimetry (DSC) endotherm curve which is substantially in accordance with FIG. 6.

The diffractogram was obtained using a Powder X-ray Diffractometer (Philips X'Pert Pro, PANalytical®) with a Cu radiation of λ=1.540598Å. The measurements were carried out from 2 degrees to 50 degrees with times per step of 50 seconds.

Figure 6:
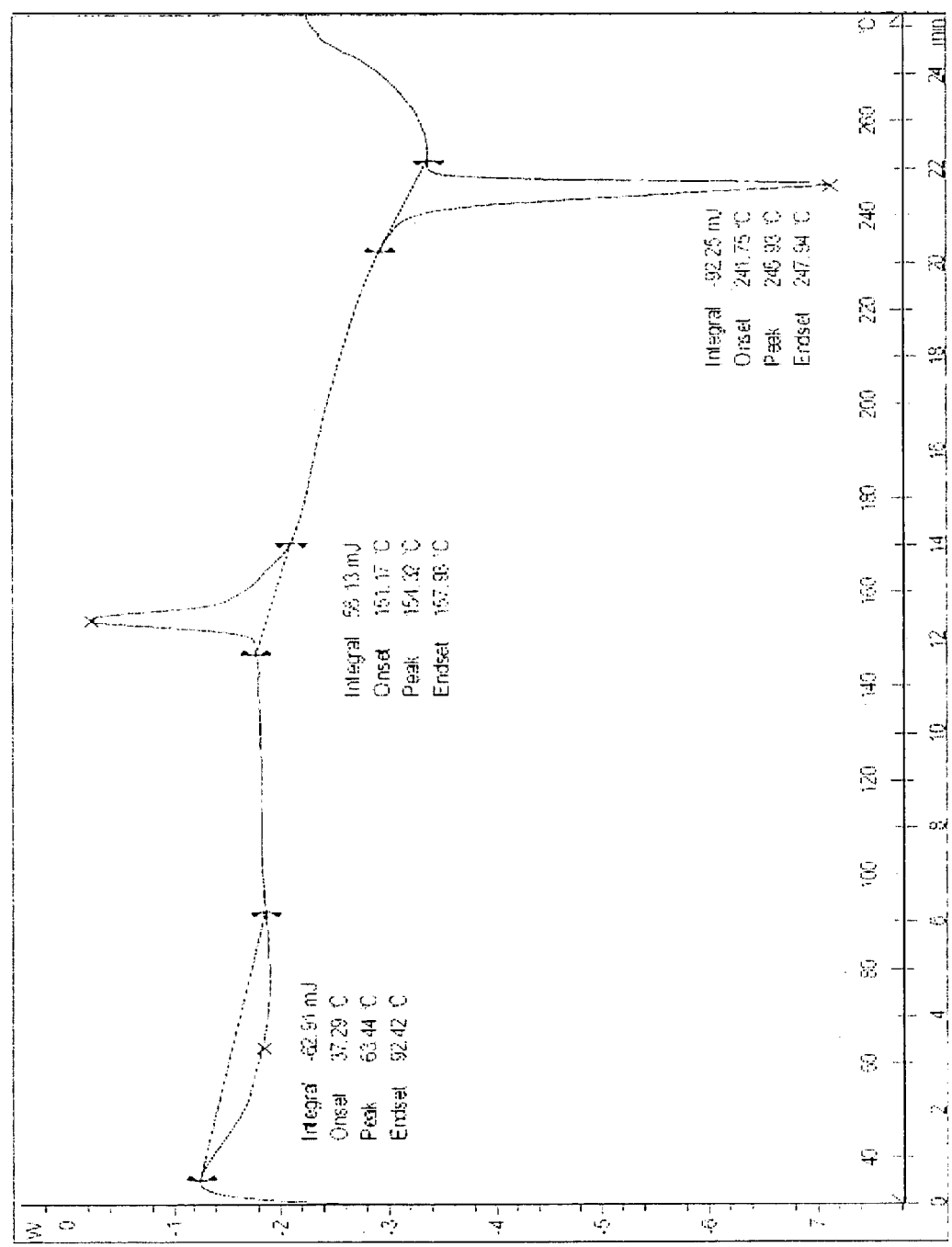
FIG. 6: Differential Scanning calorimetry (DSC) thermogram curve of a stable amorphous fosaprepitant dimeglumine, as prepared by Example 5.

Fosaprepitant dimeglumine obtained by the process of present invention is further characterized by differential scanning calorimetry (DSC) which is substantially as depicted in FIG. 6.

The DSC curves presented herein were obtained by using the method which is as follows: Approximately 1-5 mg of sample was accurately weighed into an aluminum DSC pan with lid. The sample was placed then into a Mettler Toledo DSC822$^e$ equipped with a liquid nitrogen cooling unit and allowed to equilibrate at 30° C. until stable heat flow response was seen. A dry nitrogen purge gas at a flow rate of 50 ml/min was used to produce the inert atmosphere and prevent oxidation of the sample during heating. The sample was scanned from 30° C.-350° C. at rate of 10° C./min and resulting heat flow response was measured against temperature.

The present invention provides a stable amorphous fosaprepitant dimeglumine further characterized by stability studies, which are a series of XRPD spectra, substantially in accordance with FIG. 5.

Stability is a key feature of an acceptable pharmaceutical composition. A stable pharmaceutical composition does not exhibit substantial decomposition of its active pharmaceutical ingredient (API) during the time between the manufacture of the composition and its use by a patient.

When a pharmaceutical composition comprises a heat and moisture sensitive API, which refers to a compound which rapidly degrades in the presence of heat and moisture. The stability of said API's may be improved by incorporating these compounds into lyophilized injections.

To improve the stability of such drugs, these compounds may be incorporated into lyophilized injections. The heat and moisture sensitive active pharmaceutical ingredient refers to an active pharmaceutical ingredient which rapidly degrades in the presence of heat and moisture. In understanding the term "moisture sensitive active pharmaceutical ingredient", it is helpful to study how the fosaprepitant dimeglumine obtained by the process of prior art behaves on storage. The fosaprepitant dimeglumine obtained by the lyophilization of aqueous solutions degrades at normal ambient temperatures and it is stored at −20° C. to avoid degradation, *Journal of Medicinal Chemistry.*, 2000, Vol. 43, pgs. 1234-1241, which is incorporated herein by reference.

Figure 7:
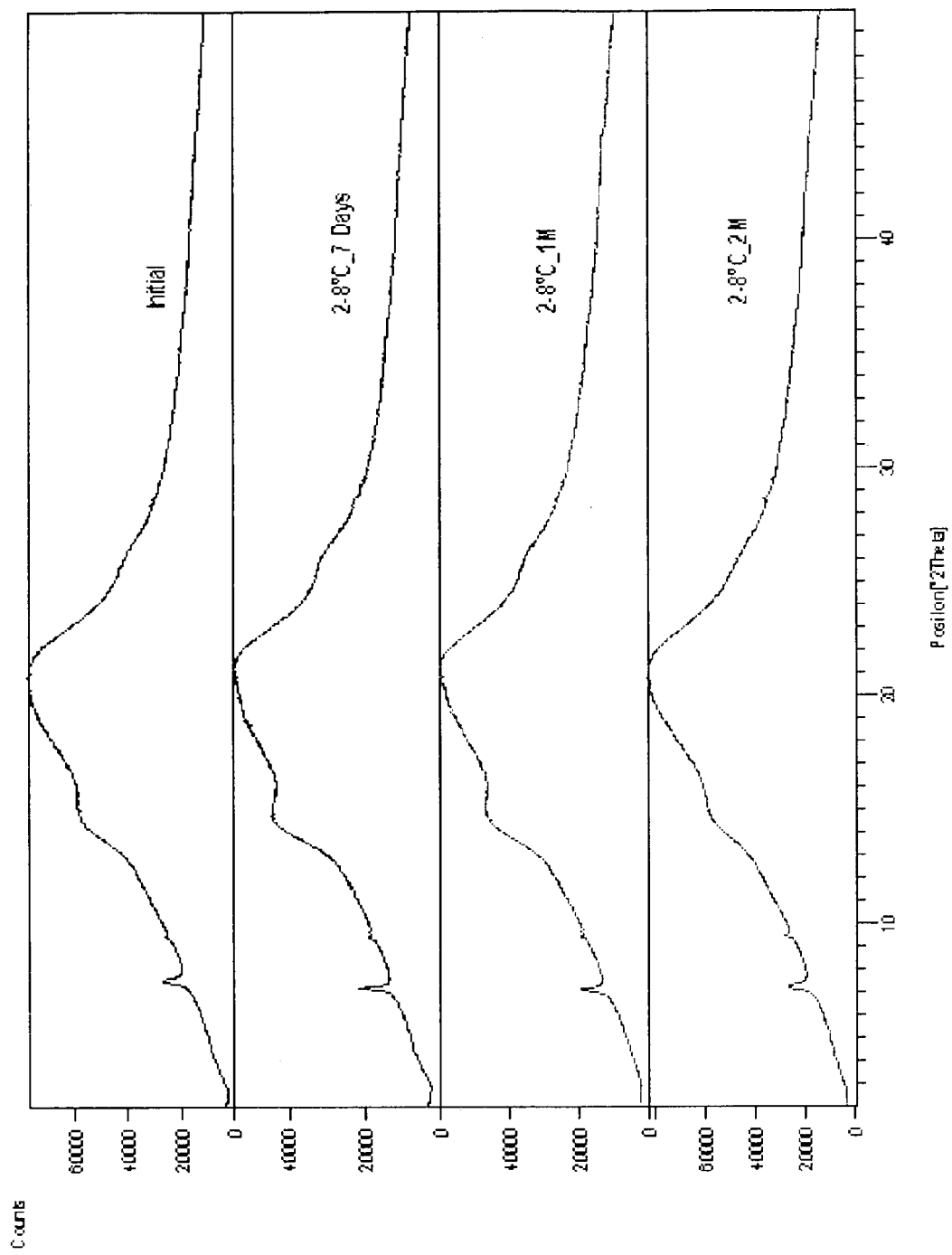
FIG. 7: Stability studies data, which are a series of XRPD spectra, of a stable amorphous fosaprepitant dimeglumine, as prepared by Example 5.

The "substantially stable amorphous fosaprepitant dimeglumine", prepared by the process herein described, is characterized by a stability profile taken at temperatures from about 2° C. to about 8° C. and relative humidity of less than about 60% for a period from about 7 days to about 2 months. The stability data, shown as series of XRPD scans, are substantially in accordance with FIG. 7. The data shows that amorphous fosaprepitant dimeglumine, prepared by the process herein described, is substantially stable, i.e., it exhibits the same polymorphic form, from the initial amorphous state in the time span of about two months.

The "stable amorphous fosaprepitant dimeglumine" as used herein, retains its amorphous form, i.e. it does not show conversion into another form of fosaprepitant dimeglumine, which is greater than 5% by weight when a) exposed to temperatures from about 2° C. to about 8° C. and relative humidity of less than about 60% for a period from about 7 days to about 2 months; or more.

It is desirable that the active pharmaceutical product should be in amorphous form to have solubility and bioavailability from the time it is formulated and consumed by the patient in need thereof. Hence it is essential to provide a stable amorphous form of fosaprepitant dimeglumine.

The amorphous fosaprepitant dimeglumine is substantially stable from about 2° C. to about 8° C. for any given period of time, retaining its amorphous nature. The substantially stable amorphous fosaprepitant dimeglumine, prepared in the manner herein described, makes it simple and easy to make suitable pharmaceutical formulations. Preferably lyophilized injections.

The process of preparing the substantially stable amorphous form of fosaprepitant dimeglumine of the present invention, which has a stability at temperatures of about 2° C. to about 8° C. and at a relative humidity below at least 60%; comprises:

a) preparing a solution of fosaprepitant dimeglumine in one or more solvents or their aqueous mixtures thereof; and optionally treating with activated carbon;

b) precipitating the solid by adding an antisolvent to the solution in a); and c) recovering the solid in b) to obtain the substantially stable amorphous fosaprepitant dimeglumine.

The suitable organic solvent(s) in a) of the process, directly described above, may be selected from water alcohols, such as methanol, ethanol, n-propanol, isopropanol, n-butanol, isobutanol, and t-butanol and the like; halogenated solvents such as dichloromethane, ethylene dichloride, chloroform and the like; aprotic polar solvents such as N,N-dimethylformamide (DMF), dimethylsulfoxide (DMSO), N,N-dimethylacetamide (DMA) and the like; or mixtures thereof in various ratios without limitation. Preferably the solvent is an alcohol; more preferably methanol.

Any solvent is acceptable for the practice of this invention as long as the fosaprepitant dimeglumine has a high enough solubility in the solvent or mixture of solvents used. The solvent system used must not cause undesirable chemical reactions with the fosaprepitant dimeglumine such as degradation under the conditions of processing to be utilized in the practice of the invention.

As used herein, a "solvent" is any liquid substance capable of dissolving fosaprepitant dimeglumine.

As used herein a "mixture of solvents" refers to a composition comprising more than one solvent.

Any temperature for dissolution in a) above, is acceptable, provided a clear solution of the concerned materials is obtained in the solvents chosen and which allows further processing of the solution to obtain the amorphous product of the invention. It will be understood that the temperatures required will also be determined by the processing conditions for the recovery of the desired final product, such as the temperature of drying, the boiling point of the solvent, the homogeneity of the solution as required after mixing solvents, the viscosity of the solution, the stability of the fosaprepitant dimeglumine, which are all within the scope of understanding of a person skilled in the art. Such variations are all included herein without any limitation.

The temperature for dissolution of fosaprepitant dimeglumine can range from about 25° C. to about 40° C. or reflux temperatures of the solvents used. Preferably, from about 25° C. to about 30° C.

The clear solution obtained is optionally filtered to remove any extraneous matter present in the solution using any standard filtration techniques known in the art.

Optionally the solvent(s) can be removed from the solution by any technique known in art which includes, for example distillation, evaporation, oven drying, tray drying, rotational drying (such as Buchi® Rotavapor), lyophilisation, spray drying, freeze-drying, fluid bed drying, flash drying, spin flash drying and ultrafilm agitated thin film dryer-vertical (ATFD-V) and the like.

The volume of the solvent used to solubilize fosaprepitant dimeglumine in a) of the process described above, may range from about 2 volumes to about 20 volumes to the weight of the fosaprepitant dimeglumine. Preferably from about 9 volumes to about 15 volumes to the weight of the fosaprepitant dimeglumine.

The antisolvents that can be used include, but are not limited to, ketones such as acetone, methyl ethyl ketone, methyl isobutyl ketone and the like; hydrocarbons such as n-hexane, n-heptane, cyclohexane and the like; ethers such as dimethyl ether, diethyl ether, diisopropyl ether and the like. Mixtures of any of these antisolvents are also contemplated. Preferably, the anti-solvent is a ketone, more preferably, acetone.

As used herein, the term "antisolvent" means a liquid in which a compound is poorly soluble. The addition of an antisolvent to a solvent reduces the solubility of a compound.

Advantageously, the volume of antisolvent used to precipitate the solid can range from about 4 volumes to 20 volumes with reference to the volume of the solvent used for solubilizing fosaprepitant dimeglumine. Preferably, from about 4 volumes to about 10 volumes of the volume of the solubilizing solvent.

The order of addition, i.e. the solubilized fosaprepitant dimeglumine to the antisolvent or the antisolvent to the solubilized fosaprepitant dimeglumine, to effectuate to precipitation of the product may vary; where the solution of fosaprepitant dimeglumine may be added to the antisolvent or vice-versa, to precipitate fosaprepitant dimeglumine.

The fosaprepitant dimeglumine used, as starting material in a) of the above process, may be of any morphology (i.e., crystalline or amorphous or mixture thereof) or may be crude fosaprepitant dimeglumine resulting from synthesis known in the art. Illustratively, U.S. Pat. No. 5,691,336 or US Publication 20070265442, which are incorporated herein by reference in their entirety, disclosed these processes.

If desired, any suspended insoluble matter may be removed by filtration or decantation.

Optionally, seeding by use of the desired polymorph is added to the solution of fosaprepitant dimeglumine to afford the desired polymorph of fosaprepitant dimeglumine.

The cooling of the precipitation reaction may be performed by reducing the temperature to about −20° C. to about ambient temperature.

In c) of the above process, the recovery of fosaprepitant dimeglumine obtained, can be performed by any conventional method, known in the art, such as filtration, decantation and centrifugation. Preferably, recovery comprises filtering, washing, and drying the solid. Washing is usually done with the same solvent used for precipitation (i.e. the antisolvent).

The product optionally may be further dried. Drying can be suitably carried out in a tray dryer, vacuum oven, air oven, fluidized bed drier, spin flash dryer, flash dryer and the like.

The temperatures for drying can range from about 25° C. to about 30° C. preferably, from about 25° C. to about 30° C.

The drying can be carried out for any desired time from about 1 hour to 80 hours, frequently being sufficient. Preferably, about 72 hours.

In yet another aspect, the present invention provides pharmaceutical compositions comprising stable amorphous form of fosaprepitant dimeglumine and one or more pharmaceutically acceptable carriers.

The resulting mixture may be manufactured in the form of a unit-dose formulation (i.e., a physically discrete unit containing a specific amount of active ingredient) such as a tablet or capsule. The pharmaceutical compositions may be in the form of suspensions, lyophilized injections.

Suitable carriers include but are not limited to fillers, binders, lubricants, inert diluents, surface active/dispersing agents, flavorants, antioxidants, bulking and granulating agents, adsorbants, preservatives, emulsifiers, suspending and wetting agents, glidants, disintegrants, buffers and pre-adjusting agents, and colorants. Examples of carriers include celluloses, modified celluloses, cyclodextrins, starches, oils, polyols, sugar alcohols and sugars, and others.

Other excipients contemplated by the present invention include binders, such as acacia gum, pregelatinized starch, sodium alginate, glucose and other binders used in wet and dry granulation and direct compression tableting processes; disintegrants such as sodium starch glycolate, crospovidone, low-substituted hydroxypropyl cellulose and others; lubricants like magnesium and calcium stearate and sodium stearyl fumarate; flavorings; sweeteners; preservatives; pharmaceutically acceptable dyes and glidants such as silicon dioxide.

The process of present invention is simple, efficient, cost effective, ecofriendly, robust, reproducible, commercially viable and industrially feasible to produce the fosaprepitant dimeglumine in stable amorphous form.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments as falling within the true spirit and scope of the present invention.

EXAMPLES

Example 1

Preparation of Dibenzylester Fosaprepitant 250 ml of tetrahydrofuran (THF), 10 gm of aprepitant and 14 gm of tetrabenzylpyrophosphate were charged into a clean and dry 4 neck round bottom flask. The reaction mixture was cooled to about −20° C. 47 ml of 1.0M sodium bis-(trimethylsilyl)amide in THF was added at about −20° C. over about 3 hours. The resultant reaction mixture was stirred for about 30 minutes. After completion of the reaction, the reaction mass was quenched by adding 250 ml of saturated sodium bicarbonate solution. 250 ml of isopropyl ether was charged and stirred for about 15 minutes. Organic and aqueous layers were separated and the organic layer washed with 250 ml of 0.5 M potassium hydrogen sulfate solution. Organic and aqueous layers were separated and the organic layer washed with 250 ml of saturated sodium bicarbonate solution. Organic and aqueous layers were separated and the organic layer was washed with 250 ml of purified water. Organic and aqueous layers were separated and the organic layer was dried over anhydrous sodium sulfate. The organic layer was distilled completely under vacuum to afford the residue. To the residue 30 ml of ethyl acetate was charged and the suspension was stirred for about 30 minutes to get a clear solution. 100 ml of cyclohexane was charged and stirred for about 2 hours. The separated solid was filtered and the solid was washed with cyclohexane. The solid (Formula (II)) obtained was dried at about 30° C. under vacuum for about 1 hour to yield 10 gm of the title compound.

Purity by HPLC: 93.74% with monobenzyl fosaprepitant (III): 1.39% and aprepitant: 1.0%, other unknown impurities: 3.83%.

Example 2

Preparation of Fosaprepitant Dimeglumine 200 ml of methanol, 10 gm of dibenzyl ester fosaprepitant of formula II obtained in example 1 and 6.0 gm of N-methyl-D-glucamine were charged in a clean and dry 4 neck round bottom flask. 2.0 gm of palladium-carbon (10%) was charged and 100 psi of anhydrous hydrogen pressure was passed for about 60 minutes under agitation. The reaction progress was monitored by HPLC. Monobenzyl impurity of formula (III) should be less than 0.1%. After completion of the reaction, the reaction suspension was filtered on celite and the celite was washed with 20 ml of methanol. The filtrate was distilled completely at about 65° C. under vacuum and 100 ml of methanol was charged. The resultant residual suspension was stirred for about 15 minutes and the solution obtained was added to 200 ml of isopropyl alcohol over about 10 minutes. The resultant reaction suspension was stirred for about 30 minutes. The separated solid was filtered and dried (Formula I) at about 30° C. under vacuum for about 1 hour to yield 8.2 gm of the title compound in crude form.

Purity by HPLC: 94.5% with dibenzyl fosaprepitant (II): Not detected, monobenzyl fosaprepitant (III): Not detected, aprepitant: 0.2%, desfluoroaprepitant: 0.08%.

Example 3

Purification of Fosaprepitant Dimeglumine 10 gm of crude Fosaprepitant dimeglumine, as obtained in example 2 and 100 ml of methanol were charged into a clean and dry 4 neck round bottom flask under nitrogen followed by stirring at about 30° C. for about 10 minutes. 300 ml of acetone (prefiltered) was charged into another clean and dry 4 neck round bottom flask. The above solution of fosaprepitant dimeglumine in methanol was added to acetone at about 25° C. over about 15 minutes under nitrogen atmosphere. The resultant reaction suspension was stirred for about 30 minutes. The separated solid was filtered under nitrogen atmosphere and the solid was washed with 50 ml of acetone. The solid (Formula I) obtained was dried at about 30° C. under vacuum for about 1 hour to yield 8 gms of the title compound in pure form.

Purity by chiral HPLC: 99.76% with Aprepitant: 0.05%; desfluoro fosaprepitant: 0.06%, monobenzyl fosaprepitant (III): below detection limit, desfluoro aprepitant: below detection limit, diastereomer of fosaprepitant: below detection limit.

All other individual impurities are below 0.05%.

Assay (on anhydrous basis): 100.5% w/w

Palladium content: below detection limit.

Content of N-methyl-D-glucamine (on anhydrous basis): 39.7% w/w.

Water content by KF: 3.2% w/w; heavy metals: less than 20 ppm.

Example 4

Fosaprepitant, Neutral Form

A) Preparation of Fosaprepitant Dimeglumine 250 ml of tetrahydrofuran and 10 gm of aprepitant was charged in a clean and dry round bottom flask followed by charging of 14 gm of tetra benzyl pyrophosphate. The resultant reaction mixture was cooled to −10° C. followed by 47 ml of the 1.0M sodium bis-(trimethylsilyl)amide solution in tetrahydrofuran (THF) was added in about 3 to 4 hours. The resultant reaction mixture was stirred for about 30 minutes. After completion of the reaction, the reaction mass was quenched by adding 250 ml of saturated sodium bicarbonate solution followed by charging of 250 ml of IPE. The reaction mass was stirred for about 15 minutes. The organic and aqueous layers were separated and the organic layer was washed with 2×250 ml of 0.5 M potassium hydrogen sulfate solution. The organic and aqueous layers were separated and the organic layer washed with 250 ml of 20% sodium chloride solution. The organic and aqueous layers were separated and the organic layer was dried on magnesium sulfate followed by distillation off of solvent under vacuum. To the residue, 125 ml of methanol and 7.0 gm of N-methyl-D-glucamine and 2.0 gm of the 10% Pd/C were charged followed by passing of 80 psi hydrogen pressure for about 120 min. The reaction was monitored by HPLC. After the completion of the reaction, the reaction suspension was filtered on hyflo filter bed and the hyflo filter bed was washed with 45 ml of methanol. The filtrate was distilled completely under vacuum followed by charging of 100 ml of methanol. The resultant residual mass was stirred for about 10-15 minutes followed by addition to 200 ml of isopropyl alcohol in about 5-10 min. The reaction contents were stirred for about 30 minutes followed by filtration of separated solid to afford 11 gm of fosaprepitant dimeglumine salt in crude form.

B) Purification of Fosaprepitant Dimeglumine 10 gm of crude fosaprepitant dimeglumine salt, prepared as in Part A, was charged into a clean and dry round bottom flask under nitrogen atmosphere, followed by charging of 100 ml of methanol. The resultant reaction contents were stirred for about 10-15 minutes. 200 ml of isopropyl alcohol was charged in another round bottom flask followed by addition of the above solution of fosaprepitant dimeglumine salt at about 25° C.-30° C. for about 15 minutes under nitrogen atmosphere. The resultant mixture was stirred at about 25° C.-30° C. for about 30 minutes. The separated solid was filtered under nitrogen atmosphere and the solid was washed with 50 ml of isopropyl alcohol and finally with 50 ml of isopropyl ether. The solid was dried at about 30° C. under nitrogen atmosphere and vacuum to afford 7.5 gm of fosaprepitant dimeglumine in amorphous form.

C) Conversion of Fosaprepitant Dimeglumine into Fosaprepitant 6.0 gm of fosaprepitant dimeglumine salt, prepared as in Part B, 120 ml of water and 120 ml of methanol were charged in a clean and dry round bottom flask followed by cooling to about 0° C. The pH of the reaction mixture was adjusted to about 1 by the addition of 1N hydrochloric acid solution at about 0° C.-5° C. The resultant reaction mixture was stirred for about 5 minutes. The separated solid was filtered and the solid was washed with copious amount of water to neutral pH. Finally, the solid was washed with 12 ml of methanol followed by drying the solid obtained at about 35° C.-40° C. under vacuum to afford 2.9 gm of fosaprepitant, neutral form, having the XRPD pattern, which is substantially in accordance with FIG. 3; and a DSC thermogram, which is substantially in accordance with FIG. 4.

Example 5

Preparation of Fosaprepitant Dimeglumine Substantially Stable Amorphous Form 10 gm of crude fosaprepitant dimeglumine and 90 ml of methanol were charged in a clean and dry 4-neck round bottom flask (RBF) under nitrogen atmosphere. The resultant reaction suspension was stirred at about 25° C.-30° C. for about 15 minutes to obtain a clear and homogenous solution. 1.0 gm of NORIT® charcoal of neutral pH was charged and the resultant suspension was stirred for about 30 min. The suspension was filtered through Celite®. And the Celite® washed with 10 ml of methanol. The filtrate was charged into a clean and dry 4 neck RBF and 350 ml of acetone was added at about 25° C.-30° C. under nitrogen atmosphere. The resultant suspension was stirred at about 25° C.-30° C. for about 30 min. The separated solid was filtered under nitrogen atmosphere and the solid was washed with 50 ml of acetone. The solid obtained was dried at about 30° C. under vacuum for 72 hours to afford the ~7.5 to 8.0 gm of the title compound.

The foregoing text describes various aspects of the invention and how the invention can be practiced. The description of the invention is not intended to provide an exhaustive description of the many different embodiments of the invention. All publications and patent applications cited above are hereby incorporated herein by reference as if each individual publication or patent application were specifically and individually indicated to be incorporated by reference. Thus, although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A process for the preparation of dibenzyl{3-[2(R)-[(1R)-1-[3,5-bis(trifluoromethyl)phenyl]ethoxy]-3(S)-(4-fluorophenyl)morpholin-4-yl}-5-oxo-4,5-dihydro-[1,2,4]-triazol-1-yl}phosphonic acid of formula (II),

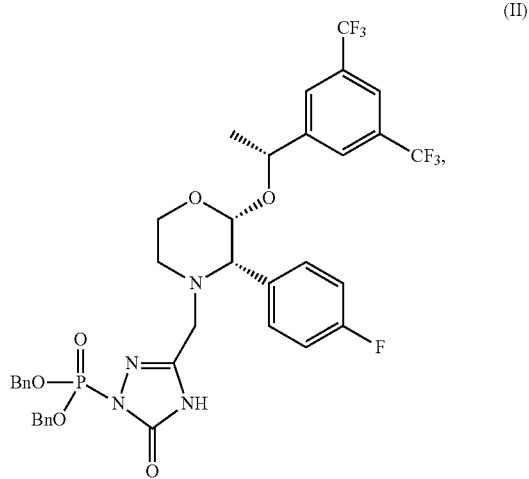 [SMILES: C[C@@H](O[C@H]1OCCN(Cc2nn(P(=O)(OCc3ccccc3)OCc3ccccc3)c(=O)[nH]2)[C@H]1c1ccc(F)cc1)c1cc(C(F)(F)F)cc(C(F)(F)F)c1]

the process comprising:
a) providing a solution of dibenzyl {3-[2(R)-[(1R)-1-[3,5-bis(trifluoromethyl)phenyl]ethoxy]-3(S)-(4-fluorophenyl)morpholin-4-yl}-5-oxo-4,5-dihydro-[1,2,4]-triazolyl}phosphonic acid in a solvent or a mixture of solvents;
b) adding an anti-solvent to the solution of (a);
c) recovering dibenzyl {3-[2(R)-[(1R)-1-[3,5-bis(trifluoromethyl)phenyl]ethoxy]-3(S)-(4-fluorophenyl)morpholin-4-yl}-5-oxo-4,5-dihydro-[1,2,4]-triazol-1-yl}phosphonic acid as a crystalline compound.

2. An isolated solid crystalline dibenzyl {3-[2(R)-[(1R)-1-[3,5-bis (trifluoromethyl)phenyl]ethoxy]-3(S)-(4-fluorophenyl) morpholin-4-yl}-5-oxo-4,5-dihydro-[1,2,4]-triazol-1-yl}phosphonic acid of formula (II)

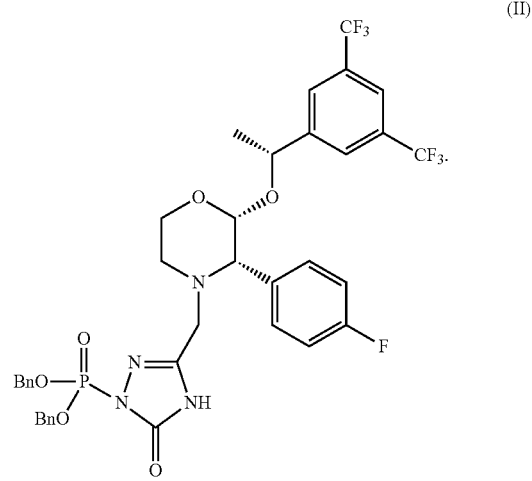 [SMILES: C[C@@H](O[C@H]1OCCN(Cc2nn(P(=O)(OCc3ccccc3)OCc3ccccc3)c(=O)[nH]2)[C@H]1c1ccc(F)cc1)c1cc(C(F)(F)F)cc(C(F)(F)F)c1]

3. An isolated dibenzyl {3-[2(R)-[(1R)-1-[3,5-bis(trifluoromethyl)phenyl]ethoxy]-3(S)-(4-fluorophenyl) morpholin-4-yl}-5-oxo-4,5-dihydro-[1,2,4]-triazol-1-yl}phosphonic acid of formula (II) in crystalline form and characterized by an X-ray diffraction powder pattern with peaks at about: 3.8, 7.5, 15.0, 16.9, 17.3, 17.6, 19.3, 20.6, 21.2, 23.9, and 24.8+0.2 degrees 2 theta

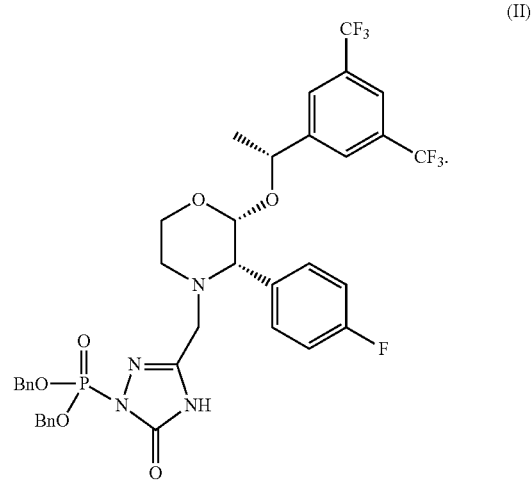 [SMILES: C[C@@H](O[C@H]1OCCN(Cc2nn(P(=O)(OCc3ccccc3)OCc3ccccc3)c(=O)[nH]2)[C@H]1c1ccc(F)cc1)c1cc(C(F)(F)F)cc(C(F)(F)F)c1]

4. The compound of claim 3, having less than about 0.5 area % of monobenzyl {3-[2(R)-[(1R)-1[3,5-bis(trifluoromethyl)phenyl]-ethoxy]-3(S)-(4-fluorophenyl)morpholin-4-yl}-5-oxo-4,5-dihydro-[1,2,4]-triazol-1-yl}phosphonic acid of formula (III), as measured by high performance liquid chromatography

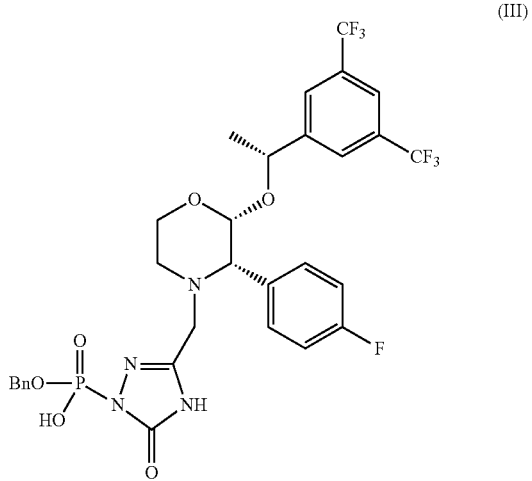 [SMILES: C[C@@H](O[C@H]1OCCN(Cc2nn(P(=O)(O)OCc3ccccc3)c(=O)[nH]2)[C@H]1c1ccc(F)cc1)c1cc(C(F)(F)F)cc(C(F)(F)F)c1]

5. The process of claim 1, wherein the solvent or mixture of solvents is selected from the group consisting of ethyl acetate, n-propyl acetate, isopropyl acetate, n-butyl acetate, isobutyl acetate, tertiary butyl acetate and mixtures thereof.

6. The process of claim 1, wherein the ratio of the dibenzyl {3-[2(R)-[(1R)-1-[3,5-bis(trifluoromethyl)phenyl]ethoxy]-3(S)-(4-fluorophenyl)morpholin-4-yl}-5-oxo-4,5-dihydro-[1,2,4]-triazolyl}phosphonic acid to the solvent is about 1:2 to 1:10.

7. The process of claim 1, wherein the anti-solvent is selected from the group consisting of n-pentane, n-hexane, n-heptane, cyclohexane or mixtures thereof.

8. The process of claim 1, wherein the ratio of the anti-solvent to the solution of (a) is about 1:4 to 1:10.

9. The process of claim 1, wherein the crystalline form of dibenzyl{3-[2(R)-[(1R)-1-[3,5-bis(trifluoromethyl)phenyl]ethoxy]-3(S)-(4-fluorophenyl) morpholin-4-yl}-5-oxo-4,5-dihydro-[1,2,4]-triazol-1-yl}phosphonic acid is characterized by an X-ray powder diffraction pattern with peaks at about: 3.8, 7.5, 15.0, 16.9, 17.3, 17.6, 19.3, 20.6, 21.2, 23.9, and 24.8+0.2 degrees 2 theta.

10. The process of claim 9, wherein the crystalline form of dibenzyl {3-[2(R)-[(1R)-1-[3,5-bis(trifluoromethyl)phenyl] ethoxy]-3(5]-(4-fluorophenyl) morpholin-4-yl}-5-oxo-4,5-dihydro-[1,2,4]-triazol-1-yl}phosphonic acid is characterized by having an X-ray powder diffraction pattern, which is substantially in accordance with FIG. 1.

11. The process of claim 1, further comprising the step of drying the crystalline compound.

12. The compound of claim 2 characterized by having an X-ray powder diffraction pattern, which is substantially in accordance with FIG. 1.

\* \* \* \* \*